United States Patent
Lim et al.

[11] Patent Number: 5,939,617
[45] Date of Patent: Aug. 17, 1999

[54] METHOD AND APPARATUS FOR TESTING THE FILTRATION EFFICIENCY OF CLOTH MATERIALS INTENDED FOR USE IN A CLEAN ROOM ENVIRONMENT

[75] Inventors: Chang-su Lim; Hyun-joon Kim; Youn-soo Han; Ok-sun Lee, all of Kyonggi-do, Rep. of Korea

[73] Assignee: Samsung Electronics Co., Ltd., Suwon, Rep. of Korea

[21] Appl. No.: 08/974,318

[22] Filed: Nov. 19, 1997

[30] Foreign Application Priority Data

Apr. 17, 1997 [KR] Rep. of Korea ................ 97-14264

[51] Int. Cl.$^6$ ................................................ G01N 15/08
[52] U.S. Cl. ................................................ 73/38
[58] Field of Search ................................................ 73/38

[56] References Cited

U.S. PATENT DOCUMENTS

| | | | |
|---|---|---|---|
| 4,382,378 | 5/1983 | Wadsworth et al. | 73/38 |
| 5,203,201 | 4/1993 | Gogins | 73/38 |

FOREIGN PATENT DOCUMENTS

| | | | |
|---|---|---|---|
| 46740 | 3/1982 | European Pat. Off. | 73/38 |
| 60-15543 | 1/1985 | Japan | 73/38 |
| 63-311145 | 12/1988 | Japan | 73/38 |
| 2233462 | 1/1991 | United Kingdom | 73/38 |

*Primary Examiner*—Daniel S. Larkin
*Attorney, Agent, or Firm*—Jones Volentine, LLP

[57] ABSTRACT

A method and an apparatus for testing the filtration efficiency of cloth materials intended for use as garments, masks, or gloves in a clean room environment where semiconductor chips are fabricated. The apparatus includes a support for holding the sample of cloth material to be tested; a gas ionizer for introducing an ionized gas into a chamber; an optional humidifier for introducing water vapor into the chamber; a particle generator for introducing particles into the chamber; and a particle counting assembly for counting the number of particles introduced into the chamber before and after they pass through the sample of cloth material being tested. Particles are introduced into the chamber after the static in the chamber has been removed by ionized gas, and the temperature and humidity in the chamber have been optionally adjusted. Filtration efficiency is determined by counting the total number of particles introduced into the chamber and the number of particles that pass through a sample of cloth material. Based on the filtration efficiency, the useful life of dust free clothes made out of the cloth material and worn by clean room operators can be determined.

25 Claims, 5 Drawing Sheets

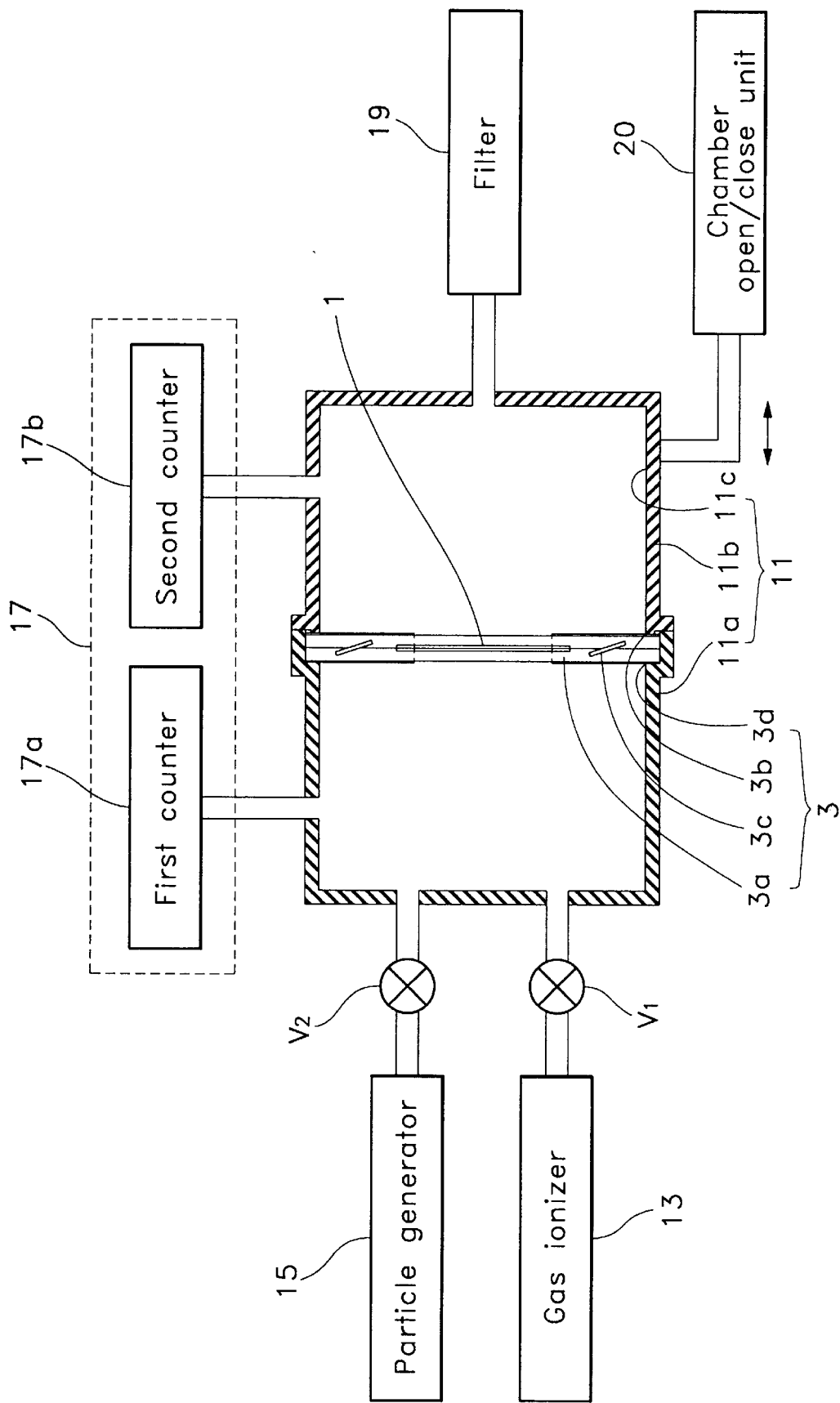

METHOD AND APPARATUS FOR TESTING THE FILTRATION EFFICIENCY OF CLOTH MATERIALS INTENDED FOR USE IN A CLEAN ROOM ENVIRONMENT

BACKGROUND OF THE INVENTION

1. Field of the Invention

The present invention relates to a method and apparatus for testing the filtration efficiency of cloth materials intended for use in a clean room environment, and further includes a method for determining the useful life of dust free clothes made from the cloth materials based on calculating the filtration efficiency of the materials.

2. Description of the Related Art

It is well known that semiconductor fabricating processes must be carried out in a clean room environment where clean air is continuously introduced. However, the presence of dust particles in the air causes contamination that may corrupt the high density and minute sized semiconductor devices. Recent efforts to improve semiconductor fabrication techniques focused on the maintenance and control of the cleanliness of the clean room by eliminating those factors that generate dust particles which adversely affect production yield, production reliability, and product quality.

Dust particles may be generated by, for example, processing equipment or expendable supplies which are used in the clean room. Clean room operators themselves are a source of particle contamination because the operator continuously generates dust by moving about the clean room as he or she works. The semiconductor chip processing equipment and the expendable supplies have been improved to the extent that they rarely generate any particle contamination. It is the operator who has become the primary source of dust particle contamination that affects the quality of semiconductor devices fabricated in a clean room environment.

Ideally, semiconductor devices should be fabricated automatically without any human intervention, however, this is impossible at the present time given the present state of the art. Therefore, efforts are continually concentrated on performing the manufacturing processes with minimum intervention by the operator, while at the same time seeking to suppress particle generation whenever human intervention is still required.

The operator working in a clean room wears dust free clothes made from cloth materials specifically designed and intended for use in a clean room environment, e.g., dust free garments, dust free masks, and dust free gloves. The ability of the material to filter, i.e. impede or block, the passage of dust particles through the material is known as filtration efficiency. To enhance the filtration efficiency of the dust free clothes worn by the operator, highly efficient cloth materials with high filtration efficiency are desirable.

As clothes made from dust free cloth age, their filtration efficiency is reduced causing them to loose their ability to filter or impede the passage of contaminating dust particles generated by body of the operator. As a result, the contaminating particles are released into the environment. Clothes made from material that has exceeded its useful life therefore become a source of particle contamination in the clean room. Accordingly, it is necessary to accurately test the filtration efficiency of the dust free clothes to determine their useful life. Similarly, the filtration efficiency of newly developed cloth materials intended for use in a clean room environment can be calculated in order to determine their suitability for such use.

Therefore, a need exists for an apparatus designed for testing the filtration efficiency of cloth materials intended for use in a clean room environment, especially one which is also suitable for use inside the clean room itself.

SUMMARY OF THE INVENTION

An object of the present invention is to provide an apparatus and method that measure the filtration efficiency of cloth material intended for use in a clean room environment where semiconductor chips are fabricated. Filtration efficiency is a measurement of the ability of a cloth material to filter, i.e., impede or block, the passage of dust particle contamination through the material. Once the filtration efficiency is known, the useful life of dust free clothes made from the cloth material can be determined. Further, measuring the filtration efficiency facilitates the design of cloth materials intended for use in a clean room environment.

To achieve these and other advantages, the present invention provides an apparatus for testing the filtration efficiency of cloth material intended for use in a clean room environment, the apparatus comprising: a support in which a sample of the cloth material to be tested is fixed and a chamber which provides a space for installation of the support and sample. The apparatus also provides a gas ionizer which generates an ionized gas and introduces the ionized gas through a first valve into the chamber to remove static from the chamber. The apparatus further provides a particle generator which generates particles and introduces the particles through a second valve into the chamber. The total number of particles introduced into the system is counted by a first particle counter which is part of the particle counting assembly. The number of particles which pass through the sample is counted by a second particle counter, also part of the particle counting assembly. In a preferred embodiment, the apparatus optionally contains a filter which filters particles exiting from the chamber of the apparatus to prevent contamination of the clean room. In another preferred embodiment, the apparatus optionally contains a humidifier which adjusts the humidity of the chamber. The temperature of the chamber can also be adjusted.

Another aspect of the present invention provides a method for calculating the filtration efficiency of a cloth material intended for use in a clean room environment. The method comprises: fixing a sample in a support, removing any static from the chamber by introducing ionized gas into the chamber, optionally adjusting the humidity in the chamber using a humidifier to introduce water vapor through a valve into the chamber, and mounting a sample of the cloth material to be tested in the chamber. After the sample is mounted in the chamber and the chamber is hermetically closed, particles are introduced into the chamber using a particle generator. The total number of particles introduced into the chamber is counted by a first particle counter at a time after all of the particles have been introduced but before any particles have passed through the sample. At a later time, which is sufficient to allow the passage of particles through the sample, a second measurement is made of the number of particles which have passed through the sample by a second particle counter. The filtration efficiency of the cloth material sample is determined from these numbers.

BRIEF DESCRIPTION OF THE DRAWINGS

The accompanying drawings illustrate embodiments of the invention, in which:

FIG. 1 is a schematic diagram of an embodiment of the apparatus for testing the filtration efficiency of cloth materials intended for use in a clean room environment according to the present invention;

DETAILED DESCRIPTION OF THE PREFERRED EMBODIMENTS

Figure 2A:
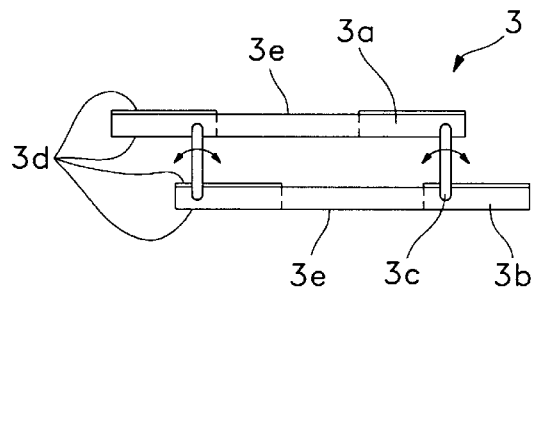
FIG. 2A and FIG. 2B are top and side views, respectively, of a support in FIG. 1 in the open position where a first plate is spaced apart from a second plate of the support.
Figure 2B:
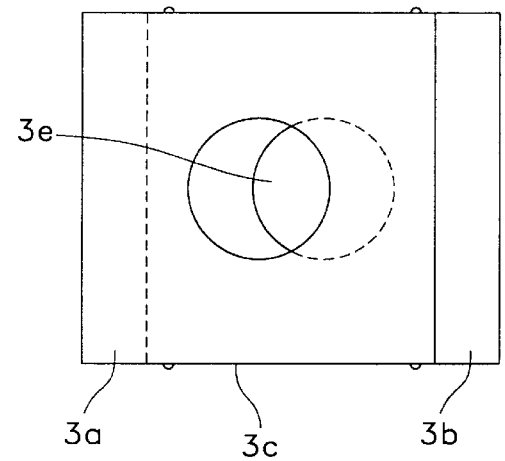
Figure 2C:
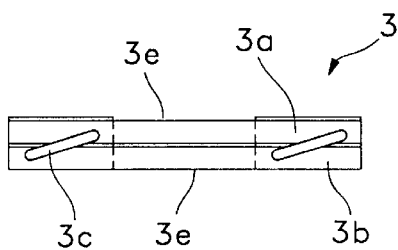
FIG. 2C and FIG. 2D are top and side views, respectively, of a support in FIG. 1 in the closed position where a first plate is in contact with a second plate of the support.
Figure 2D:
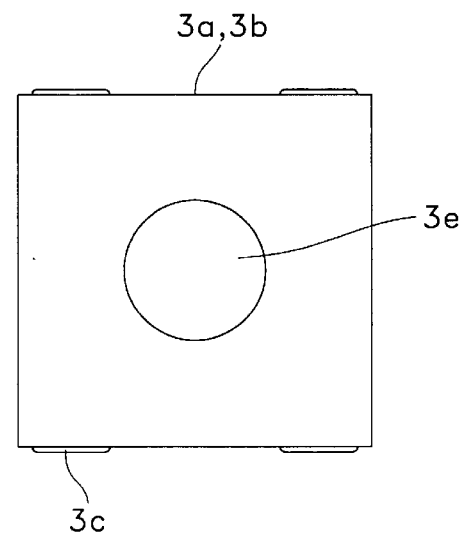

A method and apparatus for testing the filtration efficiency of cloth materials intended for use in a clean room environment according to the present invention will be hereinafter described in detail with reference to FIG. 1 through FIG. 5.

Referring to FIG. 1, the filtration testing apparatus includes a gas ionizer 13 for introducing ionized gas into a first section 11a of a chamber 11 and a particle generator 15 for introducing particles into the first section 11a of the chamber 11. A support 3 is installed between the first and the second chamber sections 11a and 11b, respectively, of the chamber 11. A particle counting assembly 17 is attached to the chamber 11 for counting the number of the particles in the chamber 11. A filter 19 is installed for filtering the particles exiting from the chamber 11. The chamber may be opened and closed to install the support and, accordingly, a chamber open/close device 20 is positioned for moving the second section 11b of the chamber 11 relative to the first section 11a. Other methods of opening/closing the chamber and installing the support are contemplated within the scope of the present invention. For example, the chamber sections may swing open. Also, the support may slide down within a space between the chamber sections.

The internal surface of the chamber 11 is coated with an anti-static film 11c. The particle counting assembly 17 includes a first particle counter 17a and a second particle counter 17b. The first particle counter 17a counts the number of the particles in the first section 11a of the chamber 11 before they pass through a sample 1 fixed to the support 3 and installed in chamber 11. The second particle counter 17b counts the number of particles in the second section 11b of the chamber 11 after they have passed through the sample 1.

As shown in FIGS. 2A through 2D, the support 3 includes a first plate 3a and a second plate 3b, each of which have a same sized central opening 3e at their respective centers. Apertures (not shown) for insertion of connecting members 3c are formed at predetermined positions on the first and the second plates 3a and 3b. The connecting members 3c connect the first plate 3a to the second plate 3b when they are inserted into the apertures. The surface of the support 3 is also coated with an anti-static film 3d. In the open position (FIGS. 2A and 2B), the respective apertures 3e have an overlapping portion, while in the closed position (FIGS. 2C and 2D), the respective apertures 3e are aligned.

The method for testing the filtration efficiency of the sample 1, i.e., a cloth material intended for use in a clean room environment, using the apparatus will be described with reference to FIG. 3.

At step S1, an operator widens the space between the first and the second plates 3a and 3b of the support 3 as shown in FIG. 2A, for insertion of the sample 1, e.g., a cloth material of a dust free garment, a dust free mask, dust free gloves, or a clean wiper for use in a clean room environment.

The first plate 3a is connected to the second plate 3b by connecting members 3c, in such a manner that one end of the connecting member 3c is inserted into an aperture (not shown) formed on the first plate 3a and the other end thereof is inserted into an aperture (not shown) formed on the second plate 3b. When the first and the second plates 3a and 3b are pushed or pulled in opposite directions, the space between the plates 3a and 3b widens and the plates are in an open position.

When the first and the second plates 3a and 3b, respectively, are in the open position, the dust free cloth material sample 1 to be tested is inserted into the space between the first and the second plates 3a and 3b, respectively, such that the sample 1 covers the central opening 3e of the plate on which it rests. To fix the sample tightly in the support 3, plates 3a and 3b are moved to the closed position shown in FIG. 2C. Note that the sample 1 must be large enough to cover the central openings 3e on the first and the second plates 3a and 3b.

At step S2, the removal step, the operator opens a valve $V_1$ of the gas ionizer 13 (see FIG. 1) thereby admitting an ionized gas into the chamber 11 in order to remove the static and any unwanted particles from the chamber 11. At this time valve $V_2$ of the particle generator 15 is closed. Suitable gas ionizers for use in the present invention are commercially available. Introducing an ionized gas into the chamber 11 removes the unwanted particles from the chamber so that accurate particle counts can be obtained for computing the filtration efficiency of the cloth material sample. Ionized gases suitable for use in the present invention include nitrogen, argon, and helium.

After introducing the ionized gas for a period of time sufficient to remove static and stray particles from the chamber 11, the number of particles remaining in the chamber is counted at step S3 using particle counter 17. The first particle counter 17a is in direct communication with the first section 11a of chamber 11, and the second particle counter 17b is in direct communication with the second section 11b of chamber 11. When the particles and the static have been completely removed, particle counters 17a and 17b will read zero. This ensures that when computing the filtration efficiency, only those particles introduced into the chamber 11 by the particle generator 15 are counted.

After making sure that the number of the particles in the chamber 11 is counted as zero in step S3, the operator proceeds to step S4. In step S4 the operator installs the support 3 in the chamber 11 while valve $V_1$ of the gas ionizer 13 remains open, thereby continuously introducing ionized gas into the chamber 11 to prevent the buildup of static or stray particles.

To install the sample of cloth material to be tested in one particular example, at step S41, the operator opens chamber 11 by moving the second section 11b of the chamber 11, which was in contact with the first section 11a, backward and away from the first section 11a using the chamber open/close device 20, e.g., an air cylinder or a driving motor. Once the chamber 11 is open, the operator installs the support 3 at a predetermined position in the chamber 11 at step S43. Step S43 is followed by step S45, in which the operator moves the second section 11*b* of the chamber 11 toward the first section 11*a* using the chamber open/close device thereby hermetically closing the chamber 11. As stated previously, other methods of installing the support and/or opening and closing the chamber are contemplated within the practice of the present invention.

Ionized gas is continuously introduced into the chamber 11 during step S4, thus preventing the open space between the first and second sections 11*a* and 11*b*, respectively, of chamber 11 from being contaminated. To be certain that no particles were introduced in the chamber 11 after installing the support, the operator may optionally recount the number of particles (step S46) in the chamber in a procedure similar to step 3, before proceeding to step 5.

At step S5, when the chamber 11 is hermetically closed, the operator closes valve $V_1$ of the gas ionizer 13 and opens valve $V_2$ of the particle generator 15. The particle generator 15 introduces particles having a predetermined size of from about 0.1 to 5.0 $\mu$m in diameter, together with nitrogen, into the first section 11*a* of the chamber 11. Pressure in chamber 11 is adjusted to a predetermined level of about 12 psi. The pressure is measured by a pressure gauge (not shown) connected to the chamber 11.

Only a small portion of the particles and nitrogen introduced into the first section 11*a* of chamber 11 actually pass through the sample 1 and enter the second section 11*b* because the sample 1 acts as a filter or barrier which impedes the passage of the particles. Consequently, a greater number of particles are retained in the first section 11*a* than pass through the sample into the second section 11*b* of chamber 11.

At step S6 the particles in the chamber are counted in two substeps. At substep 6*a*, after the particle generator 15 has introduced the particles into the first section 11*a* of the chamber 11, but before any of the particles have passed through the sample 1, the first particle counter 17*a* counts the number of particles in first section 11*a*. At a later time, which is sufficient to allow the passage of particles through the cloth material sample 1 being tested, a second measurement is made at substep 6*b* where the number of particles in the second section 11*b* of chamber 11 is counted by the second particle counter 17*b*. The results are displayed on respective displaying devices on each particle counter (not shown).

At step S7, the operator calculates the filtration efficiency of the sample 1 according to the following formula:

$$\text{Filtration efficiency } (\%)=((A-B)/A)\times 100$$

A is the total number of the particles introduced into the first section 11*a* of chamber 11, counted by particle counter 17*a* in substep 6*a*. B is the number of the particles that passed through the sample 1 into the second section 11*b* of the chamber 11, counted by particle counter 17*b* of substep 6*b*. For example, when A is 100 and B is 20, the filtration efficiency (%) is calculated as 80%.

At the end of the experiment, the particles and nitrogen remaining in the second section 11*b* are optionally passed through a filter 19 (see FIG. 1), which is in direct communication with the second section 11*b* of chamber 11. The filter 19 removes the particles and nitrogen so that no contamination is released into the clean room. The apparatus of the present invention is therefore suitable for use inside a clean room because it generates no contamination. The apparatus can optionally be used to measure filtration efficiency without the filter 19.

Figure 4:
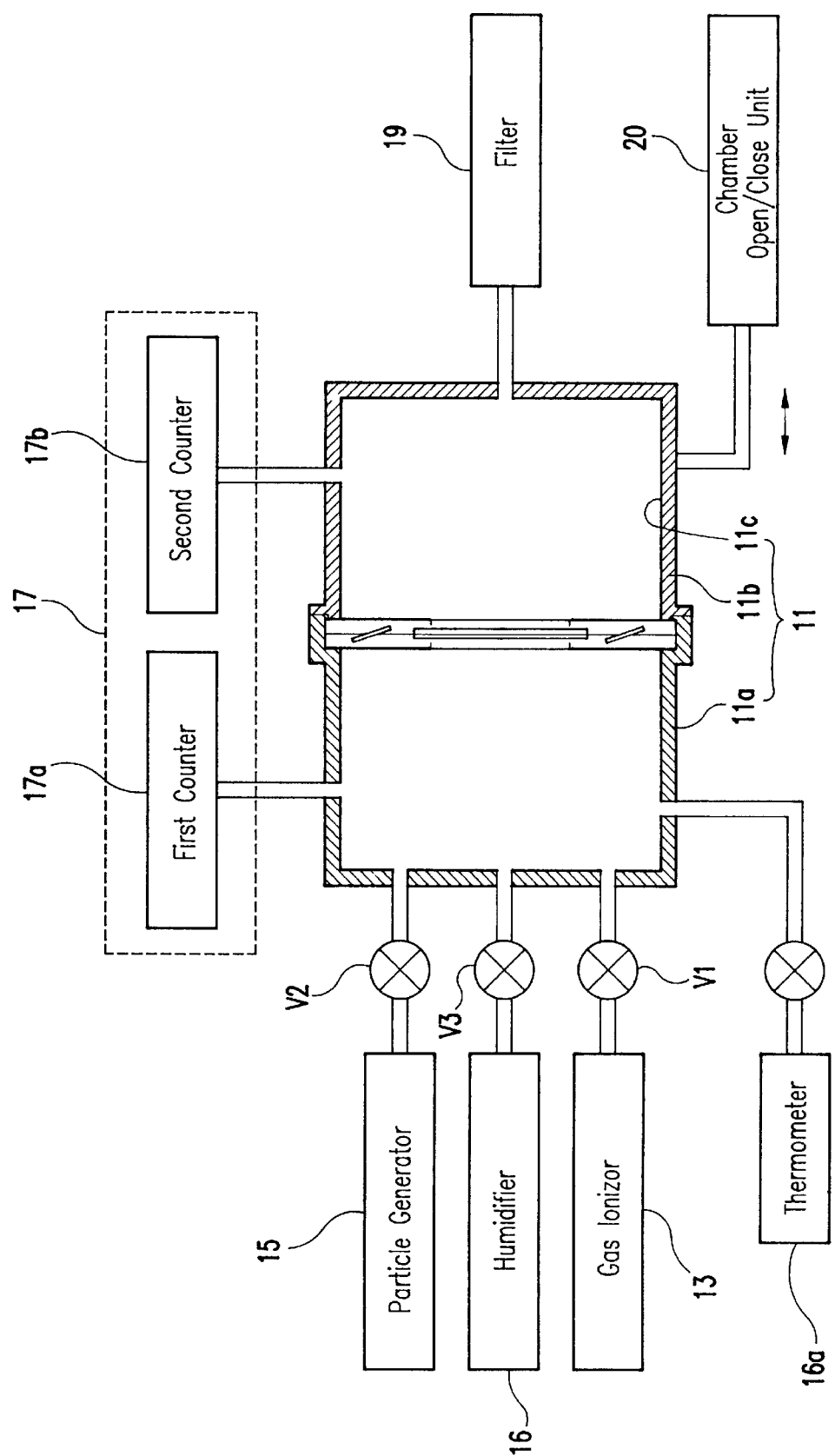
FIG. 4 is a schematic diagram of another embodiment of the apparatus for testing the filtration efficiency of cloth materials intended for use in a clean room environment wherein the apparatus of FIG. 1 further contains a humidifier.

Another embodiment of the present invention is based on the same apparatus shown in FIG. 1 except that the second embodiment, shown in FIG. 4, further includes a humidifier 16 for adjusting the humidity in the chamber 11. For description purposes, elements having basically the same function as previously described elements are identified using common reference numbers throughout the drawings.

The apparatus of FIG. 4 includes a humidifier 16 which generates water vapor that is introduced into the first section 11*a* of chamber 11 through a third valve $V_3$. The level of humidity in the chamber 11 is manipulated by opening and closing valve $V_3$.

A second method for testing the filtration efficiency of cloth materials intended for use in a clean room environment using the second apparatus with the humidifier shown in FIG. 4, is described with reference to FIG. 5.

Figure 3:
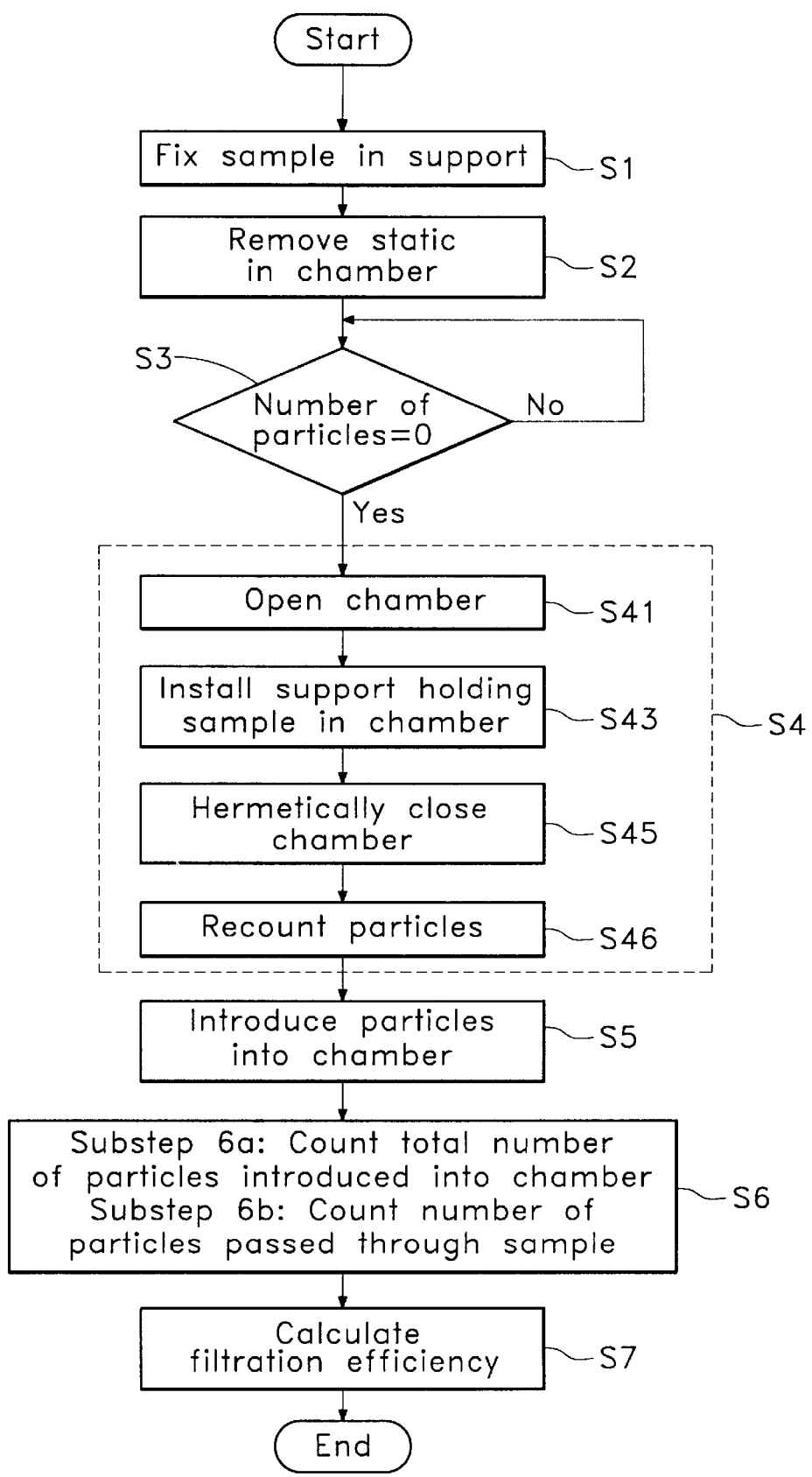
FIG. 3 is a flowchart of an embodiment of the method for testing the filtration efficiency of cloth materials intended for use in a clean room environment according to the present invention.

At step S11, a sample 1 is fixed to a support 3 in the same manner as step S1 of FIG. 3.

At step S12, the same removal process as step S2 of FIG. 3 is performed along with the additional step of adjusting the humidity in the chamber 11 by opening valve $V_3$ of the humidifier 16 to a predetermined humidity, e.g., the humidity of the clean room. To accomplish this, valve $V_3$, is opened until the humidity in the chamber 11 is the same as the humidity of the clean room, i.e., a humidity of about 45±5%. In step S12 ionized gas including but not limited to nitrogen $N_2$, argon, and helium, is introduced into the chamber 11 to remove static and any unwanted particles.

At step S13, the same counting process as step S3 of FIG. 3 is performed using particle counter 17, with the additional condition that valve $V_3$ of the humidifier 16 is open. When the particle count is zero, the operator proceeds to step S14 where the sample held in the support 3 is installed in the chamber 11. Step 14 corresponds to step S4 of FIG. 3 where valve $V_1$ of the gas ionizer 13 is open; S14 has the additional step that the valve $V_3$ of the humidifier 16 is also open.

Before proceeding to step S15, the operator may optionally count the number of particles in the chamber 11 by performing step S141 which is the same process step as S46 in FIG. 3. When the number of particles is counted as zero, the operator proceeds to step S15.

At step S15, with the chamber 11 hermetically closed, the same process as step S5 of FIG. 3 is performed under the condition that the humidity in the chamber 11 is maintained on the same level as the humidity in the clean room. As in step S5, in step S15 particle generator 15 introduces particles and nitrogen into the first section 11*a* of the chamber 11.

At steps S16 and S17, the same processes described by steps S6 and S7, respectively, in FIG. 3 are performed.

Figure 5:
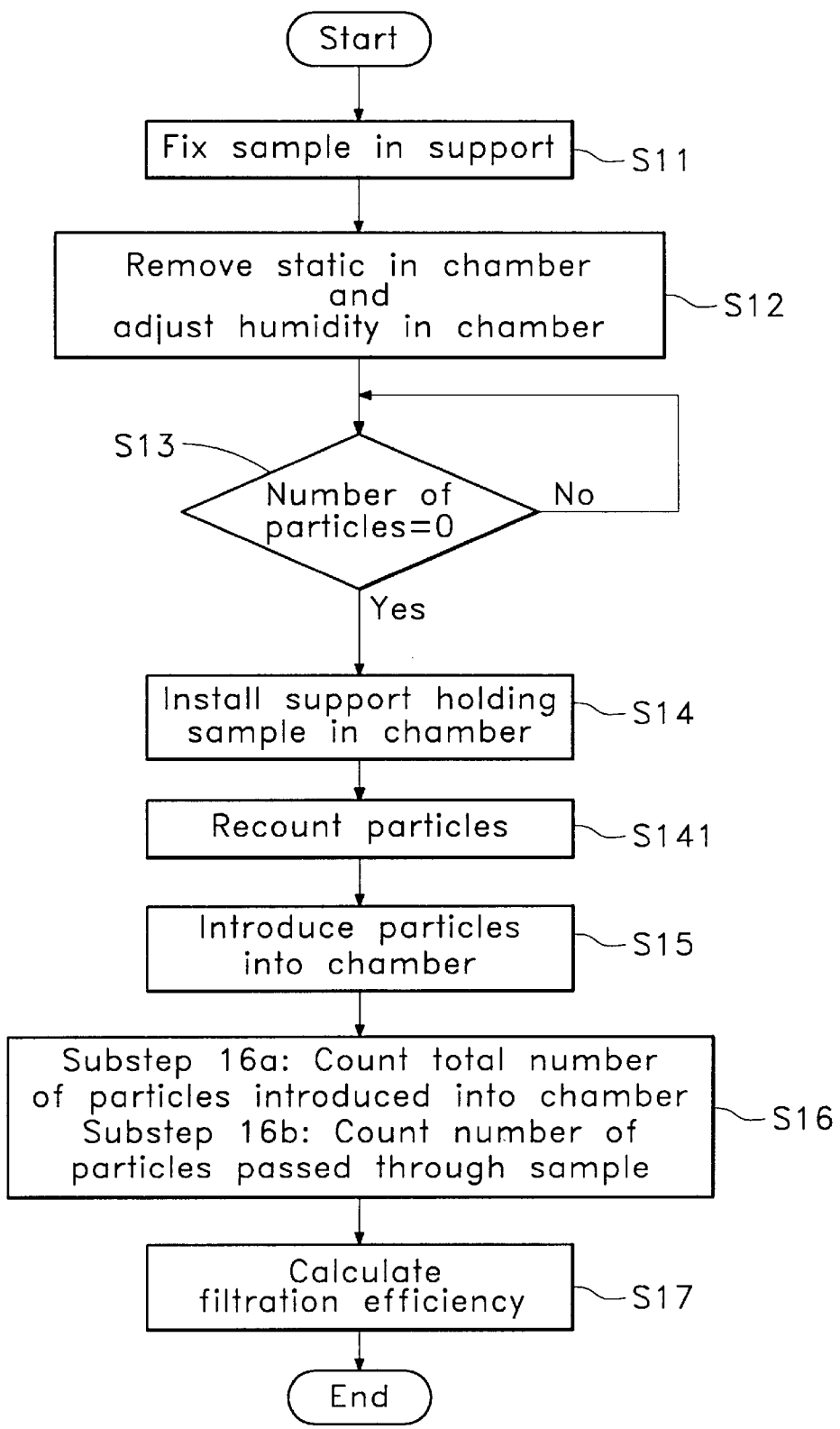
FIG. 5 is a flowchart of another embodiment of the method for testing the filtration efficiency of cloth materials intended for use in a clean room environment using the apparatus of FIG. 4.

The addition of the humidifier to the apparatus and method of FIGS. 4 and 5 permits the calculation of filtration efficiency of cloth materials intended for use in a clean room environment in an anti-static chamber having the same humidity as the clean room where these materials are to be used. The filtration efficiency is then used to accurately determine the useful life of dust free clothes made from the respective samples of cloth materials.

In another embodiment of the present invention, the temperature of the chamber 11 can be adjusted and maintained at a desired temperature using one of the many means 16*a* known to those skilled in the art.

The apparatus and method of the present invention can be used to measure the filtration efficiency of cloth materials intended for use in a clean room environment under conditions where the chamber 11 is maintained at the same temperature and humidity as the body of an operator who will wear the dust free clothes made from the materials. Measuring the filtration efficiency of cloth materials at a particular body temperature and humidity also allows the design of optimal materials for use in the clean room and the accurate determination of the useful life of dust free clothes made from the cloth materials so designed. Once the useful life of the dust free clothes is determined, it is possible to effectively prevent contaminating particles from being released from the body of the operator into the clean room by limiting the total amount of time the clothes are worn so as not to exceed the useful life of the material.

The present invention is not limited to the embodiments set forth above, and it is clearly understood that many variations may be made within the scope of the present invention by anyone skilled in the art.

What is claimed is:

1. An apparatus for testing the filtration efficiency of cloth material intended for use in a clean room environment, comprising:

a support in which a sample of cloth material to be tested is fixed;

a chamber which provides a space for installation of the support and sample;

a gas ionizer which generates an ionized gas and introduces the ionized gas through a first valve into the chamber;

a particle generator which generates particles and introduces the particles through a second valve into the chamber; and a particle counting assembly which counts the total number of particles introduced into the system by the particle generator and the number of particles which pass through the sample.

2. The apparatus of claim 1, wherein the particle counting assembly comprises:

a first particle counter in direct communication with a first section of the chamber; and a second particle counter in direct communication with a second section of the chamber.

3. The apparatus of claim 1, further comprising a filter in direct communication with a second section of the chamber which filters the particles exiting from the second section of the chamber.

4. The apparatus of claim 3, further comprising a chamber open/close device for opening and closing the chamber by moving the second section of the chamber relative to the first section of the chamber.

5. The apparatus of claim 1, further comprising a chamber open/close device for opening and closing the chamber by moving the second section of the chamber relative to the first section of the chamber.

6. The apparatus of claim 1, wherein the internal surface of the chamber is coated with an anti-static film.

7. The apparatus of claim 1, wherein the ionized gas is a member selected from the group consisting of nitrogen, argon, and helium.

8. The apparatus of claim 1, wherein the surface of the support is coated with an anti-static film.

9. The apparatus of claim 1, wherein the support comprises:

a first plate having a central opening;

a second plate having a central opening which has a same diameter as the opening in the first plate; and a means for connecting the first plate and the second plate.

10. The apparatus of claim 9, wherein the first and the second plates are contacting each other in a closed position, and the respective central openings are aligned.

11. The apparatus of claim 1, further comprising a humidifier which generates water vapor and introduces the water vapor through a third valve into the chamber.

12. The apparatus of claim 11, wherein the humidifier maintains the humidity in the chamber at the same level as the humidity of the clean room.

13. A method for testing the filtration efficiency of cloth material intended for use in a clean room environment, comprising the steps of:

fixing a sample of cloth material to a support;

removing static and unwanted particles in a chamber by introducing ionized gas into the chamber;

mounting the support holding the sample in the chamber;

introducing particles into the chamber using a particle generator;

counting the total number of particles introduced into a first section of the chamber before the particles pass through the sample using a first particle counter of a particle counting assembly in direct communication with the first section;

counting the number of particles that have passed from the first section through the sample into a second section of the chamber using a second particle counter of the particle counter assembly in direct communication with the second section; and calculating the filtration efficiency of the sample according to the counted number of the particles in first and second sections of the chamber.

14. The method of claim 13, wherein the mounting step is performed after the particle count in the removing step is zero.

15. The method of claim 14, wherein the sample fixing step includes the steps of:

widening the space between a first and a second plate of the support to place the support in an open position;

placing the sample between the first and the second plates; and bringing the first and the second plates in contact with each other in a closed position thereby tightly fixing the sample in the support.

16. The method of claim 14, wherein the support mounting step includes the steps of:

opening the chamber by moving the second section of the chamber away from the first section of the chamber using a chamber open/close device;

installing the support in the first section of the open chamber; and hermetically closing the chamber by moving the second section of the chamber toward the first section in which the support is installed using the chamber open/close device.

17. The method of claim 13, wherein after the support mounting step, the number of particles in the first section of the chamber is counted as zero by the first particle counter and the number of particles in the second section of the chamber is counted as zero by the second particle counter.

18. The method of claim 13, wherein the ionized gas continues to be introduced into the chamber during the support mounting step.

19. The method of claim 18, wherein the ionized gas continues to be introduced into the chamber even when the chamber is open.

20. The method of claim 19, wherein the ionized gas is a member selected from the group consisting of nitrogen, argon, and helium.

21. The method of claim 13, wherein the size of the particles introduced into the first section of the chamber by the particle generator is from about 0.1 to 5.0 micrometers in diameter.

22. The method of claim 13, further comprising a step of:
maintaining a humidity in the chamber at a desired level by using a humidifier to introduce water vapor through a valve into the chamber.

23. The method of claim 22, wherein the water vapor and the ionized gas continue to be introduced into the chamber even when the chamber is open.

24. The method of claim 23, wherein a temperature and the humidity in the chamber are adjusted to be the same as the body temperature and the humidity of a human.

25. The method of claim 23, wherein a temperature and the humidity in the chamber are adjusted to be the same as the temperature and the humidity of a clean room.

* * * * *